United States Patent
Henry

(10) Patent No.: US 10,325,691 B2
(45) Date of Patent: Jun. 18, 2019

(54) X-RAY BEAM ALIGNMENT DEVICE AND METHOD

(71) Applicant: Consolidated Nuclear Security, LLC, Reston, VA (US)

(72) Inventor: Nathaniel Frederick Henry, Clinton, TN (US)

(73) Assignee: Consolidated Nuclear Security, LLC, Oak Ridge, TN (US)

( * ) Notice: Subject to any disclaimer, the term of this patent is extended or adjusted under 35 U.S.C. 154(b) by 337 days.

(21) Appl. No.: 15/096,655

(22) Filed: Apr. 12, 2016

(65) Prior Publication Data

US 2017/0295633 A1 Oct. 12, 2017

(51) Int. Cl.
*A61B 6/00* (2006.01)
*A61B 6/08* (2006.01)
(Continued)

(52) U.S. Cl.
CPC .................. *G21K 1/02* (2013.01); *A61B 6/08* (2013.01); *A61B 6/547* (2013.01); *A61B 34/20* (2016.02); *A61B 90/30* (2016.02); *H01J 35/025* (2013.01); *H01J 37/228* (2013.01); *A61B 6/54* (2013.01); *A61B 6/587* (2013.01);
(Continued)

(58) Field of Classification Search
CPC ........... A61B 6/00; A61B 6/04; A61B 6/0492; A61B 6/08; A61B 6/40; A61B 6/44; A61B 6/4476; A61B 6/54; A61B 6/542; A61B 6/545; A61B 6/547; A61B 6/58; A61B 6/587; A61B 34/00; A61B 34/20; A61B 2034/309; A61B 90/30; A61B 2034/2046; A61B 2034/2055; A61B 2034/2068; A61N 5/10; A61N 5/1048; A61N 5/1049; A61N 2005/105; A61N 2005/1056; G01N 2201/00; G01N 2201/06; G01N 2201/06113; G01N 2201/0612; G01N 2201/062; G01N 2201/0623; G01N 2223/00; G01N 2223/20; G01N 2223/30; G01N 2223/323; H01J 35/00; H01J 35/02; H01J 35/025; H01J 35/22; H01J 35/226; H01J 35/228; H01J 35/3005; H01J 2237/15; H01J 2237/1501; H01J 2237/248;
(Continued)

(56) References Cited

U.S. PATENT DOCUMENTS

| | | | | | |
|---|---|---|---|---|---|
| 3,767,931 A | * | 10/1973 | Williams | .................. | A61B 6/08 378/153 |
| 6,305,842 B1 | * | 10/2001 | Kunert | ..................... | A61B 6/08 378/147 |

(Continued)

*Primary Examiner* — Anastasia Midkiff
(74) *Attorney, Agent, or Firm* — Clements Bernard Walker PLLC; Christopher L. Bernard

(57) ABSTRACT

The present invention provides a bright, focused visible light source that is part of a visible light alignment assembly that is coupled to an X-ray generator. The visible light source projects a bright, focused visible light beam from the X-ray generator through a collimator and object or part to be radiographed and to a detector or film, just as a subsequent X-ray beam eventually is. This allows the operator to quickly and easily visually assess the eventual position and coverage or spread of the X-ray beam and align the X-ray generator, collimator, object or part to be radiographed, and/or detector or film, with a minimum of test radiographs.

18 Claims, 3 Drawing Sheets

(51) Int. Cl.
*G21K 1/02* (2006.01)
*A61B 34/20* (2016.01)
*A61B 90/30* (2016.01)
*H01J 35/02* (2006.01)
*H01J 37/22* (2006.01)

(52) U.S. Cl.
CPC ............. *A61B 2034/2055* (2016.02); *G01N 2201/06113* (2013.01); *G01N 2223/323* (2013.01); *H01J 37/226* (2013.01); *H01J 2237/1501* (2013.01); *H01J 2237/2482* (2013.01)

(58) Field of Classification Search
CPC ..... H01J 2237/2482; H05G 1/00; H05G 1/02; H05G 1/08; H05G 1/26; H05G 1/30; H05G 1/52
See application file for complete search history.

(56) References Cited

U.S. PATENT DOCUMENTS

| | | | |
|---|---|---|---|
| 7,380,986 B2* | 6/2008 | Brandstatter | A61B 6/08 378/206 |
| 7,543,988 B2* | 6/2009 | Ramsauer | A61B 6/0414 378/206 |
| 7,581,885 B2* | 9/2009 | Ertel | A61B 6/08 378/204 |
| 2009/0175413 A1* | 7/2009 | Sung | A61B 6/06 378/64 |
| 2015/0036801 A1* | 2/2015 | Ohashi | G01N 23/04 378/62 |

* cited by examiner

X-RAY BEAM ALIGNMENT DEVICE AND METHOD

STATEMENT REGARDING FEDERALLY SPONSORED RESEARCH OR DEVELOPMENT

The U.S. Government has rights to the present disclosure pursuant to Contract No. DE-NA0001942 between the U.S. Department of Energy and Consolidated Nuclear Security, LLC.

FIELD OF THE INVENTION

The present invention relates generally to imaging devices and methods. More specifically, the present invention relates to an X-ray beam alignment device and method that allows for the rapid and efficient alignment of an X-ray generator and X-ray beam with a collimator, an object or part to be radiographed, and a detector or film, thereby replacing conventional mechanical and trial-and-error devices and methods.

BACKGROUND OF THE INVENTION

Conventionally, a single reflected laser beam 10 (FIGS. 1 and 2) projected from an X-ray generator 12 (FIGS. 1 and 2) is used to approximate the centerline of a projected X-ray beam through a collimator 14 (FIGS. 1 and 2) and object or part to be radiographed 16 (FIGS. 1 and 2) and to a detector or film 18 (FIGS. 1 and 2). This allows for the approximate alignment of the X-ray generator 12, but does not provide an accurate estimate of X-ray beam coverage or spread. Similarly, a string tied to the face of the X-ray generator 12 may be used to "string in" a radiograph. These devices and methods require a significant amount of operator skill and experience, and do not always result in satisfactory results due to various environmental factors. Often, several estimations and test radiographs are required to determine the correct alignment of the X-ray generator 12, collimator 14, object or part to be radiographed 16, and detector or film 18, given the X-ray beam coverage or spread. This is slow and inefficient, and wastes physical resources (i.e., film, developer, and fixer).

Thus, what is still needed in the art is an X-ray beam alignment device and method that allows for the rapid and efficient alignment of an X-ray generator 12 and X-ray beam with a collimator 14, an object or part to be radiographed 16, and a detector or film 18, thereby replacing conventional mechanical and trial-and-error devices and methods.

BRIEF SUMMARY OF THE INVENTION

In various exemplary embodiments, the present invention provides a bright, focused visible light source 20 (FIGS. 1 and 2) that is part of a visible light alignment assembly 22 (FIGS. 1 and 2) that is coupled to the X-ray generator 12. The visible light source 20 projects a bright, focused visible light beam 24 (FIG. 2) from the X-ray generator 12 directly through the collimator 14 and object or part to be radiographed 16, without reflection, and to the detector or film 18 (FIGS. 1 and 2), just as the subsequent X-ray beam eventually would be. The visible light beam 24 and the subsequent X-ray beam are projected along the same linear path. This allows the operator to quickly and easily visually assess the eventual position and coverage or spread of the X-ray beam and align the X-ray generator 12, collimator 14, object or part to be radiographed 16, and/or detector or film 18, with a minimum of test radiographs. The visible light alignment assembly 22 preferably includes an interlock mechanism that prevents the visible light beam 24 and the X-ray beam from being deployed simultaneously. Further, the visible light alignment assembly 22 may include a visual and/or auditory alert device that alerts the operator that the visible light beam 24 is deployed prior to the operator exiting the radiography vault, for example. As is described in greater detail herein below, the visible light source 20 can include a light-emitting diode (LED) or the like and the interlock mechanism can include a frame 26 coupled to the face of the X-ray generator 12 including a hinge 28 and a switch mechanism 30, such that the visible light beam 24 is disabled when the visible light source 20 is positioned away from the front of the X-ray generator 12 and enabled when the visible light source 20 is positioned close to the front of the X-ray generator 12, for example.

Specifically, in one exemplary embodiment, the present invention provides an X-ray system, comprising: an X-ray generator operable for selectively projecting an X-ray beam to the vicinity of a detector along a projection path; and a visible light source coupled to the X-ray generator operable for selectively projecting a visible light beam to the vicinity of the detector along the projection path; wherein, when projected, the visible light beam initially illuminates an intersection area of the projection path in a vicinity of the detector such that an alignment of one or more of the X-ray generator, the detector, and an intervening component can be determined and a position and/or size of the intersection area of the projection path in the vicinity of the detector can be adjusted, if necessary, for subsequent X-ray beam projection. The X-ray system further comprising a collimator disposed along the projection path. The X-ray system further comprising one or more of an object and a part to be imaged disposed along the projection path. The X-ray system further comprising an interlock mechanism that selectively disables the X-ray generator from projecting the X-ray beam when the visible light source is projecting the visible light beam. The X-ray system further comprising an interlock mechanism that selectively disables the visible light source from projecting the visible light beam when the X-ray generator is projecting the X-ray beam. The X-ray system further comprising one or more translation mechanisms for translating one or more of the X-ray generator and the detector relative to one another. The X-ray system further comprising one or more of a visual alarm mechanism and an auditory alarm mechanism that is activated when the visible light source is projecting the visible light beam. The X-ray system further comprising a target surface coupled to the detector to which the visible light beam is projected by the visible light source.

Specifically, in another exemplary embodiment, the present invention provides an X-ray beam alignment device for aligning one or more components of an X-ray system comprising an X-ray generator operable for selectively projecting an X-ray beam to the vicinity of a detector along a projection path, the X-ray beam alignment device comprising: a visible light source coupled to the X-ray generator operable for selectively projecting a visible light beam to the vicinity of the detector along the projection path; wherein, when projected, the visible light beam initially illuminates an intersection area of the projection path in a vicinity of the detector such that an alignment of one or more of the X-ray generator, the detector, and an intervening component can be determined and a position and/or size of the intersection area of the projection path in the vicinity of the detector can be adjusted, if necessary, for subsequent X-ray beam projection. The X-ray beam alignment device wherein the X-ray system further comprises a collimator disposed along the projection path. The X-ray beam alignment device wherein the X-ray system further comprises one or more of an object and a part to be imaged disposed along the projection path. The X-ray beam alignment device further comprising an interlock mechanism that selectively disables the X-ray generator from projecting the X-ray beam when the visible light source is projecting the visible light beam. The X-ray beam alignment device further comprising an interlock mechanism that selectively disables the visible light source from projecting the visible light beam when the X-ray generator is projecting the X-ray beam. The X-ray beam alignment device further comprising one or more translation mechanisms for translating one or more of the X-ray generator and the detector relative to one another. The X-ray beam alignment device further comprising one or more of a visual alarm mechanism and an auditory alarm mechanism that is activated when the visible light source is projecting the visible light beam. The X-ray beam alignment device further comprising a target surface coupled to the detector to which the visible light beam is projected by the visible light source.

Specifically, in a further exemplary embodiment, the present invention provides an X-ray beam alignment method, comprising: selectively projecting a visible light beam from a visible light source coupled to an X-ray generator to a vicinity of a detector along a projection path through one or more intervening components and/or objects, wherein the visible light beam initially illuminates an intersection area of the projection path in the vicinity of the detector; selectively adjusting the alignment of one or more of the X-ray generator, the detector, and the one or more intervening components and/or objects such that a position and/or size of the intersection area of the projection path in the vicinity of the detector is adjusted; and selectively projecting an X-ray beam from the X-ray generator to the vicinity of the detector along the projection path through the one or more intervening components and/or objects. The X-ray beam alignment method wherein the one or more intervening components and/or objects comprise a collimator disposed along the projection path. The X-ray beam alignment method wherein the one or more intervening components and/or objects comprise a part disposed along the projection path. The X-ray beam alignment method further comprising providing an interlock mechanism that selectively disables the X-ray generator from projecting the X-ray beam when the visible light source is projecting the visible light beam. The X-ray beam alignment method further comprising providing an interlock mechanism that selectively disables the visible light source from projecting the visible light beam when the X-ray generator is projecting the X-ray beam. The X-ray beam alignment method further comprising providing one or more translation mechanisms for translating one or more of the X-ray generator, the detector, and the one or more intervening components and/or objects relative to one another. The X-ray beam alignment method further comprising providing one or more of a visual alarm mechanism and an auditory alarm mechanism that is activated when the visible light source is projecting the visible light beam. The X-ray beam alignment method further comprising providing a target surface coupled to the detector to which the visible light beam is projected by the visible light source.

BRIEF DESCRIPTION OF THE DRAWINGS

The present invention is illustrated and described herein with reference to the various drawings, in which like reference numbers are used to denote like device components/method steps, as appropriate, and in which.

DETAILED DESCRIPTION OF THE INVENTION

Figure 1:
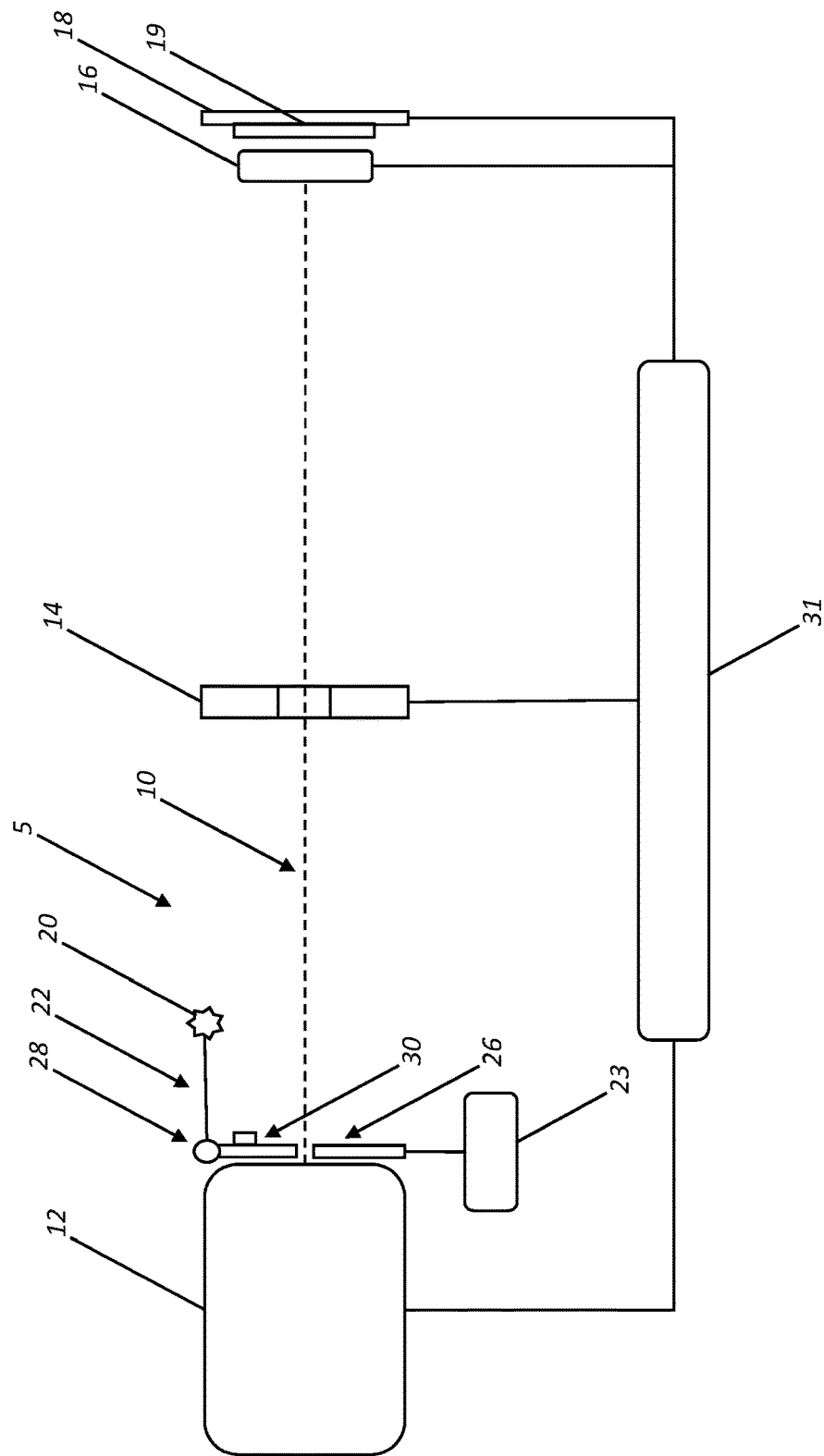
FIG. 1 is a schematic diagram illustrating one exemplary embodiment of the X-ray beam alignment device 5 and method of the present invention, with the visible light source 20 in a disabled position and the visible light beam 24 turned off.
Figure 2:
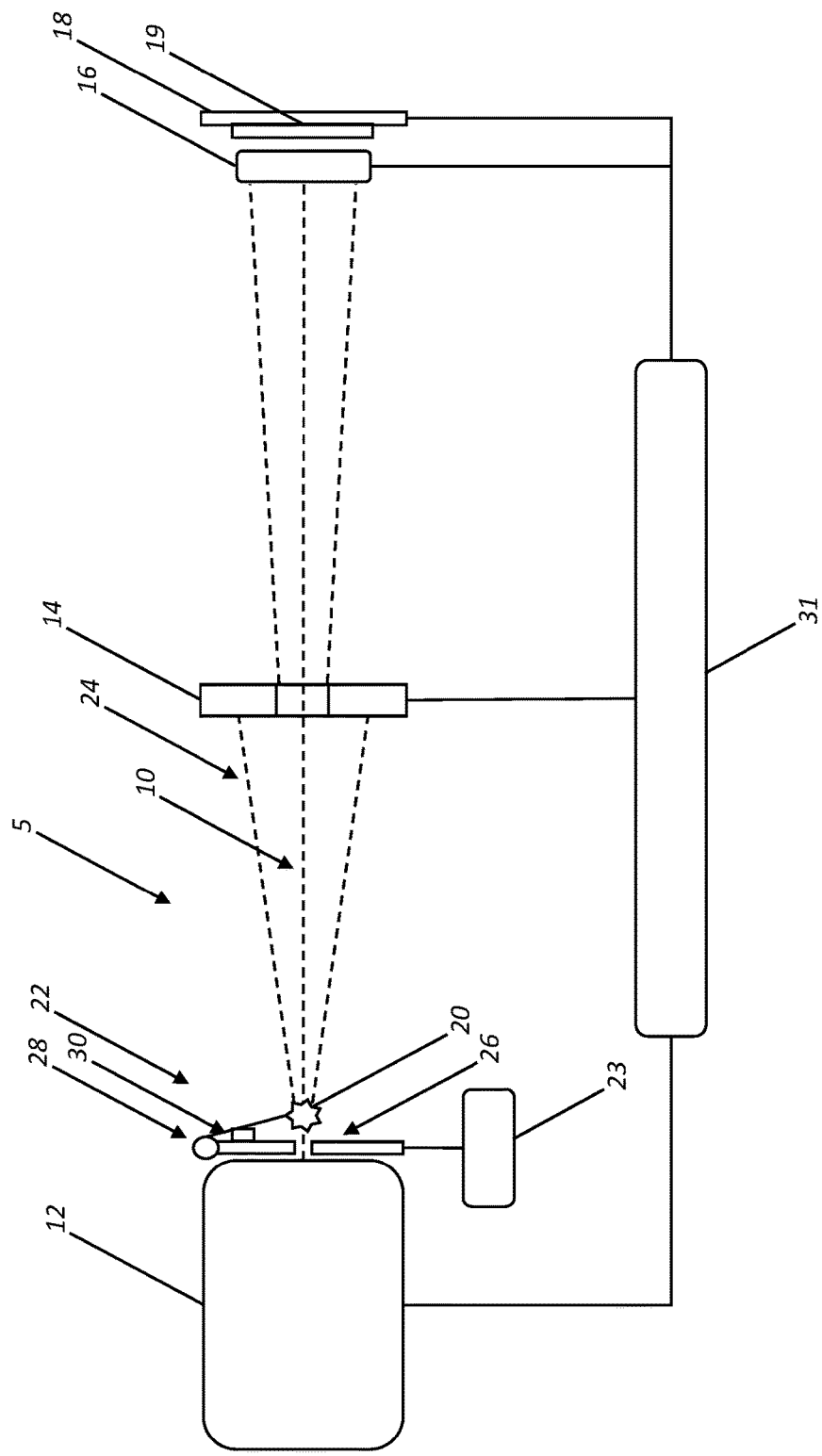
FIG. 2 is another schematic diagram illustrating one exemplary embodiment of the X-ray beam alignment device 5 and method of the present invention, with the visible light source 20 in an enabled position and the visible light beam 24 turned on such that X-ray beam alignment can be performed.

Referring now specifically to FIGS. 1 and 2, the present invention provides a bright, focused visible light source 20 that is part of the visible light alignment assembly 22 that is coupled to the X-ray generator 12—optionally, the face of the X-ray generator 12. The visible light source 20 projects a bright, focused visible light beam 24 (FIG. 2) from the face of the X-ray generator 12 through the collimator 14 and object or part to be radiographed 16 and to the detector or film 18, just as the subsequent X-ray beam eventually would be. This allows the operator to quickly and easily visually assess the eventual position and coverage or spread of the X-ray beam at the detector or film 18 and align the X-ray generator 12, collimator 14, object or part to be radiographed 16, and/or detector or film 18, with a minimum of test radiographs.

As will be apparent to those of ordinary skill in the art, the X-ray generator 12 typically includes an X-ray tube in which X-ray photons are produced by an electron beam that is accelerated to a very high speed and strikes a target. The electrons that make up the beam are emitted from a heated cathode filament. The electrons are then focused and accelerated by an electrical field towards an angled anode target. The point where the electron beam strikes the target is called the focal spot. Most of the kinetic energy contained in the electron beam is converted to heat and dissipated via a heat sink, but around 1% of the energy is converted into X-ray photons. At the focal spot, X-ray photons are emitted in all directions from the target surface, the highest intensity being around 60° to 90° from the beam due to the angle of the anode target to the approaching electron beam. There is a small round window in the X-ray tube directly above the angled target. This window allows the X-ray to exit the tube with little attenuation while maintaining a vacuum seal required for the X-ray tube operation. X-ray machines work by applying controlled voltage and current to the X-ray tube, which results in a beam of X-rays. The beam is projected on matter. Some of the X-ray beam will pass through the object, while some is absorbed. The resulting pattern of the radiation is then ultimately detected by a detection medium including rare earth screens (which surround photographic film), semiconductor detectors, or X-ray image intensifiers.

As will also be apparent to those of ordinary skill in the art, the collimator 14 typically filters a stream of X-rays so that only those traveling parallel to a specified direction are allowed through. Collimators are used in X-ray optics because it is not yet typically feasible to focus radiation with such short wavelengths into an image through the use of lenses as is routine with electromagnetic radiation at optical or near-optical wavelengths.

As will further be apparent to those of ordinary skill in the art, related to the detector or film 18, imaging detectors for radiography were originally photographic plates and X-ray film (i.e., photographic film) but are now mostly replaced by various digitizing devices, such as image plates or flat panel detectors. The first radiographs (i.e., X-ray images) were made by the action of X-rays on sensitized glass photographic plates. X-ray film (i.e., photographic film) soon replaced the glass plates, and film has been used for decades to acquire (and display) medical and industrial images. Gradually, digital computers gained the ability to store and display enough data to make digital imaging possible. Since the 1990s, computerized radiography and digital radiography have been replacing photographic film in medical and dental applications, though film technology remains in widespread use in industrial radiography processes (e.g., to inspect welded seams). The metal silver (formerly necessary to the radiographic and photographic industries) is a non-renewable resource, although silver can easily be reclaimed from spent X-ray film. Whereas X-ray films required wet processing facilities, these new technologies do not. The digital archiving of images utilizing these new technologies also saves storage space. Thus it is beneficial that film use is being phased out. Because photographic plates are sensitive to X-rays, they provide a means of recording the image, but they also require much X-ray exposure (to the patient, for example). The addition of a fluorescent intensifying screen (or screens) in close contact with the film allows a lower dose to the patient, for example, because the screen(s) improve the efficiency of X-ray detection, making more activation of the film from the same amount of X-rays, or the same activation of the film from a smaller amount of X-rays. An alternative method is the use of photostimulated luminescence (PSL), pioneered by Fuji in the 1980s. In modern hospitals, for example, a photostimulable phosphor plate (PSP plate) is used in place of the photographic plate. After the plate is X-rayed, excited electrons in the phosphor material remain 'trapped' in 'colour centres' in the crystal lattice until stimulated by a laser beam passed over the plate surface. The light given off during laser stimulation is collected by a photomultiplier tube, and the resulting signal is converted into a digital image by computer technology, which gives this process its common name, computed radiography. The PSP plate can be reused, and existing X-ray equipment requires no modification to use them. X-rays are also used in "real-time" procedures, such as angiography or contrast studies of the hollow organs, for example, using fluoroscopy acquired using an X-ray image intensifier. Since the 1970s, semiconductor detectors have been developed (silicon or germanium doped with lithium: Si(Li) or Ge(Li)). X-ray photons are converted to electron-hole pairs in the semiconductor and are collected to detect the X-rays. When the temperature is low enough (the detector is cooled by Peltier effect or even cooler liquid nitrogen), it is possible to directly determine the X-ray energy spectrum; this method is called energy dispersive X-ray spectroscopy (EDX or EDS); it is often used in small X-ray fluorescence spectrometers. These detectors are sometimes called "solid state detectors." Detectors based on cadmium telluride (CdTe) and its alloy with zinc, cadmium zinc telluride, have an increased sensitivity, which allows lower doses of X-rays to be used. Practical application in medical imaging started in the 1990s. Currently, amorphous selenium is used in commercial large area flat panel X-ray detectors for mammography and chest radiography, for example. Silicon drift detectors (SDDs), produced by conventional semiconductor fabrication, now provide a cost-effective and high resolving power radiation measurement. Unlike conventional X-ray detectors, such as Si(Li), they do not need to be cooled with liquid nitrogen. Some materials, such as sodium iodide (NaI), can "convert" an X-ray photon to a visible photon; an electronic detector can be built by adding a photomultiplier. These detectors are called "scintillators", filmscreens, or "scintillation counters." The main advantage of using these is that an adequate image can be obtained while subjecting the object or part to be imaged to a much lower dose of X-rays. In order to gain energy spectrum information, a diffracting crystal may be used to separate the different photons. This method is called wavelength dispersive X-ray spectroscopy (WDX or WDS). Position-sensitive detectors are often used in conjunction with dispersive elements. Other detection equipment that is inherently energy-resolving may be used, such as the aforementioned proportional counters. In either case, use of suitable pulse-processing (MCA) equipment allows digital spectra to be created for later analysis. With the advent of large semiconductor array detectors, it has become possible to design detector systems using a scintillator screen to convert from X-rays to visible light, which is then converted to electrical signals in an array detector. Indirect flat panel detectors (FPDs) are in widespread use today in medical, dental, veterinary, and industrial applications. The array technology is a variant on the amorphous silicon TFT arrays used in many flat panel displays, like the ones in computer laptops. The array consists of a sheet of glass covered with a thin layer of silicon that is in an amorphous or disordered state. At a microscopic scale, the silicon has been imprinted with millions of transistors arranged in a highly ordered array, like the grid on a sheet of graph paper. Each of these thin-film transistors (TFTs) is attached to a light-absorbing photodiode making up an individual pixel (i.e., picture element). Photons striking the photodiode are converted into two carriers of electrical charge, called electron-hole pairs. Since the number of charge carriers produced will vary with the intensity of incoming light photons, an electrical pattern is created that can be swiftly converted to a voltage and then a digital signal, which is interpreted by a computer to produce a digital image. Although silicon has outstanding electronic properties, it is not a particularly good absorber of X-ray photons. For this reason, X-rays first impinge upon scintillators made from such materials as gadolinium oxysulfide or caesium iodide. The scintillator absorbs the X-rays and converts them into visible light photons that then pass onto the photodiode array.

Figures 3A, 3B:
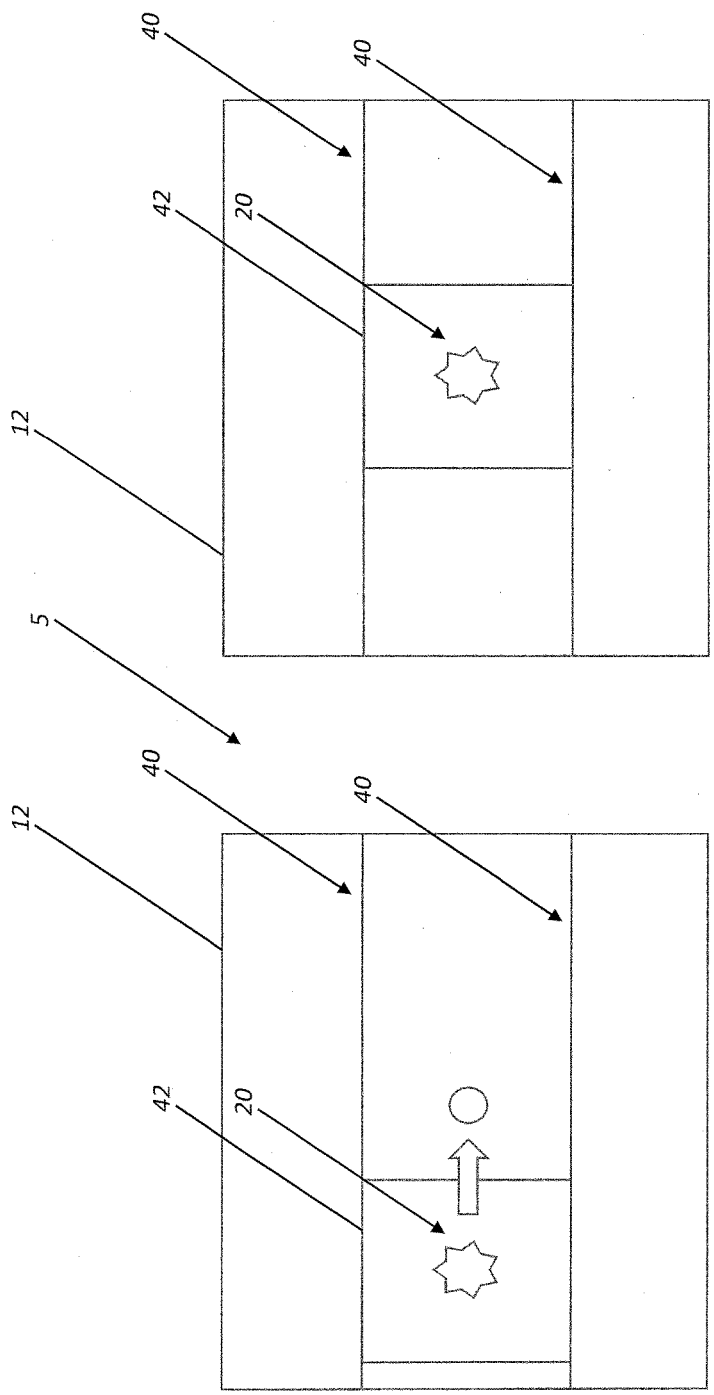
FIGS. 3a and 3b are schematic diagrams illustrating another exemplary embodiment of the X-ray beam alignment device 5 and method of the present invention.

The visible light alignment assembly 22 preferably includes an interlock mechanism that prevents the visible light beam 24 and the X-ray beam from being deployed simultaneously. Further, the visible light alignment assembly 22 may include a visual and/or auditory alert device 23 that alerts the operator that the visible light beam 24 is deployed prior to the operator exiting the radiography vault, for example. The visible light source 20 can include a light-emitting diode (LED) or other suitable high-intensity light source. The interlock mechanism can include a frame 26 coupled to the face of the X-ray generator 12 including a hinge 28 and a switch mechanism 30, such that the visible light beam 24 is disabled when the visible light source 20 is positioned away from the front of the X-ray generator 12 and enabled when the visible light source 20 is positioned close to the front of the X-ray generator 12, for example. For example, referring now specifically to FIGS. 3*a* and 3*b*, the interlock mechanism can include parallel slide rails 40 or the like coupled to the face of the X-ray generator 12 for sliding a slide plate 42 or the like in front of and away from the front of the X-ray generator 12, and to which slide plate 42 the visible light source 20 is attached for positioning in front of the X-ray generator 12 and to which slide plate 42 the switch mechanism 30 (FIGS. 1 and 2) is attached such that the visible light beam 24 is disabled when the visible light source 20 is positioned away from the front of the X-ray generator 12 and enabled when the visible light source 20 is positioned close to the front of the X-ray generator 12. Finally, and again referring now to FIGS. 1 and 2 one or more of the X-ray generator 12, the collimator 14, the object or part to be radiographed 16, and the detector or film 18 and target surface 19 may be coupled to a translation stage 31 for adjusting the alignment of the various components while the visible light beam 24 is utilized, and one or more projection screens may be inserted into the visible light beam 24 at various points for visualization purposes.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following non-limiting claims.

What is claimed is:

1. An X-ray system, comprising:
    an X-ray generator operable for selectively projecting an X-ray beam to a detector along a linear projection path; and
    a visible light alignment assembly coupled to the X-ray generator and operable for selectively projecting a visible light beam from a visible light source directly towards the detector along the linear projection path;
    wherein, when projected, the visible light beam initially illuminates an intersection area of the linear projection path and the detector such that an alignment of one or more of the X-ray generator, the detector, and an intervening component comprising one or more of a collimator and an imaged object can be determined and a position and/or size of the intersection area of the linear projection path and the detector can be adjusted, if necessary, for subsequent X-ray beam projection; and
    wherein the X-ray generator is operable for projecting the X-ray beam directly to the detector along the linear projection path subsequent to the visible light alignment assembly projecting the visible light beam from the visible light source directly towards the detector along the linear projection path by selectively moving the visible light source from a position adjacent to an intersection of a face of the X-ray generator and the linear projection path to a position away from the linear projection path.

2. The X-ray system of claim 1, further comprising an interlock mechanism that selectively disables the X-ray generator from projecting the X-ray beam when the visible light source is projecting the visible light beam.

3. The X-ray system of claim 1, further comprising an interlock mechanism that selectively disables the visible light source from projecting the visible light beam when the X-ray generator is projecting the X-ray beam.

4. The X-ray system of claim 1, further comprising one or more translation mechanisms for translating one or more of the X-ray generator and the detector relative to one another.

5. The X-ray system of claim 1, further comprising one or more of a visual alarm mechanism and an auditory alarm mechanism that is activated when the visible light source is projecting the visible light beam.

6. The X-ray system of claim 1, further comprising a target surface coupled to the detector to which the visible light beam is projected by the visible light source.

7. An X-ray beam alignment device for aligning one or more components of an X-ray system comprising an X-ray generator operable for selectively projecting an X-ray beam to a detector along a linear projection path, the X-ray beam alignment device comprising:
    a visible light alignment assembly coupled to the X-ray generator and operable for selectively projecting a visible light beam from a visible light source directly towards the detector along the linear projection path;
    wherein, when projected, the visible light beam initially illuminates an intersection area of the linear projection path and the detector such that an alignment of one or more of the X-ray generator, the detector, and an intervening component comprising one or more of a collimator and an imaged object can be determined and a position and/or size of the intersection area of the linear projection path and the detector can be adjusted, if necessary, for subsequent X-ray beam projection; and
    wherein the X-ray generator is operable for projecting the X-ray beam directly to the detector along the linear projection path subsequent to the visible light alignment assembly projecting the visible light beam from the visible light source directly towards the detector along the linear projection path by selectively moving the visible light source from a position adjacent to an intersection of a face of the X-ray generator and the linear projection path to a position away from the linear projection path.

8. The X-ray beam alignment device of claim 7, further comprising an interlock mechanism that selectively disables the X-ray generator from projecting the X-ray beam when the visible light source is projecting the visible light beam.

9. The X-ray beam alignment device of claim 7, further comprising an interlock mechanism that selectively disables the visible light source from projecting the visible light beam when the X-ray generator is projecting the X-ray beam.

10. The X-ray beam alignment device of claim 7, further comprising one or more translation mechanisms for translating one or more of the X-ray generator and the detector relative to one another.

11. The X-ray beam alignment device of claim 7, further comprising one or more of a visual alarm mechanism and an auditory alarm mechanism that is activated when the visible light source is projecting the visible light beam.

12. The X-ray beam alignment device of claim 7, further comprising a target surface coupled to the detector to which the visible light beam is projected by the visible light source.

13. An X-ray beam alignment method, comprising:
    first, selectively projecting a visible light beam from a visible light source of a visible light alignment assembly coupled to an X-ray generator directly towards a detector along a linear projection path through an intervening component comprising one or more of a collimator and an imaged object, wherein the visible light beam initially illuminates an intersection area of the linear projection path and the detector;
    selectively adjusting the alignment of one or more of the X-ray generator, the detector, and the intervening component such that a position and/or size of the intersection area of the linear projection path and the detector is adjusted;
second, moving the visible light source away from the linear projection path; and
third, selectively projecting an X-ray beam from the X-ray generator directly towards the detector along the linear projection path through the intervening component.

14. The X-ray beam alignment method of claim 13, further comprising providing an interlock mechanism that selectively disables the X-ray generator from projecting the X-ray beam when the visible light source is projecting the visible light beam.

15. The X-ray beam alignment method of claim 13, further comprising providing an interlock mechanism that selectively disables the visible light source from projecting the visible light beam when the X-ray generator is projecting the X-ray beam.

16. The X-ray beam alignment method of claim 13, further comprising providing one or more translation mechanisms for translating one or more of the X-ray generator, the detector, and the one or more intervening components and/or objects relative to one another.

17. The X-ray beam alignment method of claim 13, further comprising providing one or more of a visual alarm mechanism and an auditory alarm mechanism that is activated when the visible light source is projecting the visible light beam.

18. The X-ray beam alignment method of claim 13, further comprising providing a target surface coupled to the detector to which the visible light beam is projected by the visible light source.

* * * * *